(12) United States Patent
Piechowiak

(10) Patent No.: US 11,558,700 B2
(45) Date of Patent: Jan. 17, 2023

(54) METHODS OF ESTIMATING EAR GEOMETRY AND RELATED HEARING DEVICES

(71) Applicant: GN HEARING A/S, Ballerup (DK)

(72) Inventor: Tobias Piechowiak, Ballerup (DK)

(73) Assignee: GN HEARING A/S, Ballerup (DK)

( * ) Notice: Subject to any disclaimer, the term of this patent is extended or adjusted under 35 U.S.C. 154(b) by 268 days.

(21) Appl. No.: 16/033,605

(22) Filed: Jul. 12, 2018

(65) Prior Publication Data

US 2019/0076058 A1 Mar. 14, 2019

(30) Foreign Application Priority Data

Sep. 13, 2017 (EP) .................................... 17190783

(51) Int. Cl.
*H04R 25/00* (2006.01)
*A61B 5/107* (2006.01)
*A61B 5/12* (2006.01)
*A61B 5/00* (2006.01)

(52) U.S. Cl.
CPC .......... *H04R 25/652* (2013.01); *A61B 5/1073* (2013.01); *A61B 5/1075* (2013.01); *A61B 5/12* (2013.01); *A61B 5/6803* (2013.01); *H04R 25/505* (2013.01); *H04R 25/604* (2013.01); *H04R 25/70* (2013.01); *H04R 2225/025* (2013.01); *H04R 2225/83* (2013.01)

(58) Field of Classification Search
CPC ....... A61B 5/1073; A61B 5/1075; A61B 5/12; A61B 5/6803; A61B 5/1072; A61B 5/1076; A61B 5/1077; H04R 25/70; H04R 25/652; H04R 25/604; H04R 25/505; H04R 2225/83; H04R 2225/025; H04R 25/407; H04R 25/658; H04R 31/00
See application file for complete search history.

(56) References Cited

U.S. PATENT DOCUMENTS

| 6,792,114 | B1 | 9/2004 | Kates et al. |
| 8,045,737 | B2 | 10/2011 | Stirnemann |
| 9,374,638 | B2 | 6/2016 | Petersen |
| 2007/0036377 | A1 | 2/2007 | Stirnemann |

(Continued)

FOREIGN PATENT DOCUMENTS

| EP | 1594344 A2 | 11/2005 |
| EP | 1594344 A3 | 3/2006 |

(Continued)

OTHER PUBLICATIONS

Extended European Search Report dated Feb. 20, 2018 for corresponding European Application No. 17190783.5, 7 Pages.

(Continued)

*Primary Examiner* — Allen Porter
*Assistant Examiner* — Abid A Mustansir
(74) *Attorney, Agent, or Firm* — Vista IP Law Group, LLP

(57) ABSTRACT

A method for estimating an ear geometry of an ear of a user with a hearing device, the hearing device comprising an ear canal microphone, an external microphone, and a receiver, includes: obtaining an external input signal using the external microphone; providing an output signal by the receiver; obtaining an ear canal microphone input signal using the ear canal microphone; and estimating the ear geometry based on the external input signal and the ear canal microphone input signal.

28 Claims, 3 Drawing Sheets

(56) References Cited

U.S. PATENT DOCUMENTS

2014/0321657 A1 10/2014 Stirnemann
2015/0172839 A1 6/2015 Rung

FOREIGN PATENT DOCUMENTS

| EP | 2 234 414 A2 | 9/2010 |
| EP | 2 234 414 A3 | 1/2012 |
| EP | 2 744 227 A1 | 6/2014 |
| WO | WO 2013/075255 A1 | 5/2013 |

OTHER PUBLICATIONS

Non-Final Office Action dated Mar. 13, 2018 for related U.S. Appl. No. 15/703,708.
Final Office Action dated Mar. 5, 2019 for related U.S. Appl. No. 15/703,708.
Advisroy Action Office Action dated Jun. 13, 2019 for related U.S. Appl. No. 15/703,708.
Non-Final Office Action dated Jun. 28, 2019 for related U.S. Appl. No. 15/703,708.
Final Office Action dated Jan. 28, 2020 for related U.S. Appl. No. 15/703,708.
Advisroy Action Office Action dated Jun. 18, 2020 for related U.S. Appl. No. 15/703,708.
Non-final Office Action dated Jul. 27, 2020 for co-pending related U.S. Appl. No. 15/703,708.
Communication Pursuant to Article 94 (3) dated Jan. 27, 2020 for corresponding European Application No. 17 190 783.5.
Scheperele, Rachel A et al "Further Assessment of Forward Pressure Level for in Situ Calibration" The journal of the acoustical society of America, vol. 130, No. 6, Dec. 2011, pp. 3882-3892.

METHODS OF ESTIMATING EAR GEOMETRY AND RELATED HEARING DEVICES

RELATED APPLICATION DATA

This application claims priority to, and the benefit of, European Patent Application No. 17190783.5 filed on Sep. 13, 2017. The entire disclosure of the above application is expressly incorporated by reference herein.

FIELD

The present disclosure relates to methods of estimating ear geometry of an ear of a hearing device user with a hearing device and related hearing devices.

BACKGROUND

Hearing device manufacturers have adopted laser scanning of traditional impressions as the method of obtaining representations of the ear geometry. A dispenser acquires the impression from the patient and sends the impression directly to the manufacturer. Unfortunately, the impression can become distorted during the mailing process due to uncured material and excessive temperatures in the delivery trucks. This results an inaccurate impression of the patient's ear geometry, which in turn leads to a hearing device that does not fit properly mechanically and acoustically.

SUMMARY

Accordingly, there is a need for hearing devices capable of and methods for estimating an ear geometry of an ear of a hearing device user with a hearing device, which overcome or mitigate the disadvantages presented above.

A method for estimating an ear geometry of an ear of a hearing device user with a hearing device is disclosed. The hearing device comprises an ear canal microphone, an external microphone and a receiver. The method comprises: obtaining an external input signal with the external microphone; transmitting an output signal with the receiver. The method comprises obtaining an ear canal microphone input signal using the ear canal microphone; and estimating the ear geometry based on the external input signal and the ear canal microphone input signal.

Further, a hearing device is provided, the hearing device comprising: a set of microphones comprising an external microphone for provision of an external input signal, and an ear canal microphone for obtaining an ear canal microphone input signal; a processor for processing input signals and providing a processed output signal based on input signals; and a receiver for transmission of an output signal. The hearing device may comprise a controller configured to control hearing device settings. The hearing device is configured to estimate the ear geometry based on the external input signal and the ear canal microphone input signal.

It is an advantage of the present disclosure that the ear geometry, such as an ear canal geometry, can be estimated without having to scan the ear, prepare and send an impression to the manufacturer. This reduces significantly the likelihood of errors to propagate in the process of fitting acoustically the hearing device to the hearing device user. The fitting process at the dispenser comprises adjusting the processing of signals in the hearing device to the ear geometry of the hearing device user. Estimation of the ear geometry enables further improvement in providing a hearing device that acoustically fits the individual ear and optimizes processing of signals in the hearing device, for e.g. active noise cancellation, beamforming, compression.

A method for estimating an ear geometry of an ear of a user with a hearing device, the hearing device comprising an ear canal microphone, an external microphone, and a receiver, includes: obtaining an external input signal using the external microphone; providing an output signal by the receiver; obtaining an ear canal microphone input signal using the ear canal microphone; and estimating the ear geometry based on the external input signal and the ear canal microphone input signal.

Optionally, the act of estimating the ear geometry comprises: predicting an output response based on the external input signal and gain setting(s) of the hearing device; determining a difference between the predicted output response and the ear canal microphone input signal; and estimating the ear geometry based on the difference.

Optionally, the act of estimating the ear geometry comprises categorizing an ear canal.

Optionally, the act of estimating the ear geometry comprises determining one or more ear canal parameters.

Optionally, the one or more ear canal parameters comprises one or more of an ear canal volume, an ear canal width, an ear canal length, and an ear canal conicity.

Optionally, the one or more ear canal parameter is determined based on an estimate of real-ear unaided gain, and/or user input.

Optionally, the act of obtaining the external input signal comprises determining one or more characteristics of a signal.

Optionally, the act of obtaining the external input signal comprises determining one or more characteristics of a signal in one or more frequency bands.

Optionally, the act of obtaining the ear canal microphone input signal comprises generating the ear canal microphone input signal by the ear canal microphone Optionally, the ear canal microphone input signal is generated in response to the output signal received by the ear canal microphone.

Optionally, the act of obtaining the ear canal microphone input signal comprises determining a forward pressure level of the ear canal microphone input signal.

Optionally, the act of determining the difference between the predicted output response and the ear canal microphone input signal is performed based on one or more hearing device configuration parameters.

Optionally, the act of determining the difference between the predicted output response and the ear canal microphone input signal is performed based on an initial hearing device calibration setting.

Optionally, the receiver is in an ear canal part of the hearing device.

Optionally, the act of obtaining the external input signal is performed in response to a measurement signal provided by an external device.

A hearing device includes: a receiver for providing of an output signal; an external microphone for providing an external input signal; an ear canal microphone for providing an ear canal microphone input signal; and a processing unit configured to estimate an ear geometry based on the external input signal and the ear canal microphone input signal.

Optionally, the processing unit is configured to estimate the ear geometry by: predicting an output response based on the external input signal and gain setting(s) of the hearing device; determining a difference between the predicted output response and the ear canal microphone input signal; and estimating the ear geometry based on the difference.

Optionally, the processing unit is configured to determine the difference between the predicted output response and the ear canal microphone input signal based on one or more hearing device configuration parameters.

Optionally, the processing unit is configured to determine the difference between the predicted output response and the ear canal microphone input signal based on an initial hearing device calibration setting.

Optionally, the processing unit is configured to estimate the ear geometry by categorizing an ear canal and/or determining one or more ear canal parameters.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
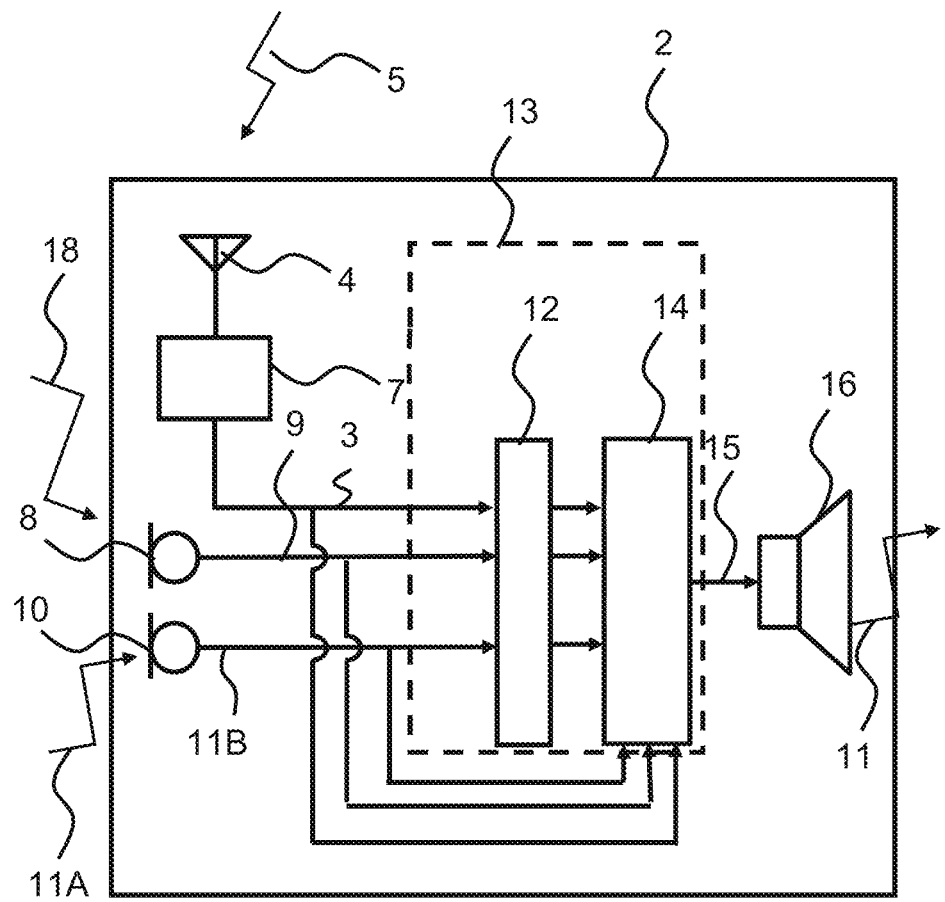
FIG. 1 schematically illustrates an exemplary hearing device according to this disclosure, FIG. 2 schematically illustrates a cross-section of an exemplary hearing device partly inserted in an ear canal of a user of a hearing device.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The inventors have found that pinna is responsible for most of the variations in insertion-gain (& directional cues) across individuals, and an ear canal microphone (placed in the ear canal) actually captures most of these variations. Inventors have found that residual variance is due to the length resonance of the ear canal which is direction-independent and varies less across individuals. The present disclosure permits to find a good approximation of these individual resonances (i.e., looking at the feedback path), and thereby obtain an improved estimation of the ear geometry.

A method for estimating an ear geometry of an ear of a hearing device user with a hearing device is disclosed. The ear geometry may refer to the geometry of the ear canal. The hearing device comprises an ear canal microphone, an external microphone and a receiver. The method is performed at the hearing device. The method may be seen to relate to estimating ear geometry of an ear of the hearing device user having the hearing device placed in the ear. The method comprises obtaining an external input signal with the external microphone.

In one or more exemplary methods, obtaining an external input signal with the external microphone comprises measuring the external input signal using the external microphone. For example, obtaining an external input signal with the external microphone comprises measuring the external input signal using the external microphone and analysing the external input signal.

The method comprises transmitting an output signal with the receiver. In other words, the receiver takes as input the output signal and emits an audio output signal based on the output signal.

The method comprises obtaining an ear canal microphone input signal using the ear canal microphone. In one or more exemplary methods, the hearing device may comprise one or more ear canal microphones and obtaining an ear canal microphone input signal may be performed using the one or more ear canal microphones. The ear canal microphone input signal may be a specific measurement signal and/or an environmental signal. The measured ear canal microphone input signal may be denoted as an ear canal microphone input signal indicative of the output signal as the measured ear canal microphone input signal relates to the output signal as measured at the ear canal microphone and taken as input in the ear canal microphone. The ear canal microphone input signal may be seen as the output signal affected by the ear canal properties. The present disclosure allows quantifying the transformation of the output signal transmitted based on the measured ear canal microphone input signal (e.g. indicative of the measured output signal), which in turn results in estimation of the ear geometry.

The method comprises estimating the ear geometry based on the external input signal and the ear canal microphone input signal. The ear geometry may refer to an ear shape, ear canal dimensions, and/or properties the ear or ear canal in space. In one or more exemplary methods, the ear geometry may comprise ear dimensions, and/or ear canal type.

In one or more exemplary methods, estimating ear geometry comprises predicting an output response based on the external input signal and gain settings of the hearing device. Estimating ear geometry may comprise determining a difference between the predicted output response and the ear canal microphone input signal. Estimating ear geometry may comprise estimating the ear geometry based on the difference. Determining the difference between the predicted output response and the ear canal microphone input signal may be seen as calculating an error between the predicted output response and the measured ear canal microphone input signal. In one or more exemplary methods, determining the difference between the predicted output response and the measured output signal may comprise estimating other parameters of the ear canal, such as one or more tympanic membrane properties. Determining the difference between the predicted output response and the ear canal microphone input signal may take into account ear canal dimensions and/or hearing device configurations.

In one or more exemplary methods, estimating the ear geometry comprises categorizing an ear, such as categorizing an ear canal. For example, one or more categories may be predetermined, and possibly stored in the hearing device. A category may index one or more parameters indicative of the ear geometry or the ear canal geometry. A plurality of categories may lead to more accuracy in estimating the ear geometry. Categorizing an ear or an ear canal may be performed based on the ear canal parameter. Categorizing an ear or an ear canal may comprise identifying an ear canal type indicative of the present ear or ear canal under test. It may also be seen that categorizing an ear or an ear canal comprises estimating the ear geometry. For example, one of the one or more ear canal parameters is estimated, resulting in a categorization of the ear/ear canal. Once the category is identified, additional ear canal parameters associated with the category can be obtained.

In one or more exemplary methods, estimating the ear geometry comprises determining one or more ear canal parameters. In one or more exemplary methods, the one or more ear canal parameters comprise one or more of an ear canal length, an ear canal width, a conicity of the ear canal, and an ear canal volume. The one or more ear canal parameters may comprise an insertion depth of the ear canal microphone and/or of the receiver. In one or more exemplary methods, determining the ear canal parameter is based on an estimate of real-ear unaided gain, user input and/or acoustic measurement. For example, determining the ear canal parameter may be based on an analysis of the measured signals and the predicted output signal. For example, the input and output signals (measured by the two microphones) may be compared to estimate ear canal parameters. In determining the difference between the predicted output response and the ear canal microphone input signal, the inventors have determined that a length resonance often results in a spectral notch in the output ear canal microphone input signal at the ear canal microphone, and the frequency of this notch varies with the residual ear canal length. The ear canal length can thereby be determined. Once the frequency of the notch of the output ear canal microphone input signal at the ear canal microphone is identified, a canal length that is expected to result in a notch at this frequency is determined using the category. An appropriate real-ear insertion gain (REIG) correction for an ear canal under test may be determined based on an expected spectral difference between the locations of the ear canal microphone and the tympanic membrane. To correct the insertion gain, the method may comprise applying the inverse of the predicted real-ear insertion gain (assuming target gain is 0 dB). It may be envisaged that as predictions are not perfect, a fraction of the predicted real-ear insertion gain may be used as a conservative correction.

In one or more exemplary methods, estimating the ear geometry comprises predicting an output response based on the external input signal and gain settings, determining a difference between the predicted output response and the ear canal microphone input signal, and estimating the ear geometry based on the difference. In one or more exemplary methods, predicting the output response may be performed based on gain settings of the hearing device and/or device calibration of the hearing device (such as factory or default device calibration). Such a device calibration is performed during design/manufacturing, based on an ear simulator and/or average ear. Device calibration may include a coupler response for flat-insertion gain (CORFIG), which is a correction that is applied to the output of a hearing-aid in order to provide a flat gain when the hearing device is inserted. A standard CORFIG may be based on an average ear and thus may represent a standard measure that does not account for individual differences in ear canal geometry.

In one or more exemplary methods, determining a difference between the predicted output response and the ear canal microphone input signal comprises determining a difference between the predicted output magnitude spectrum of predicted output response and the measured output magnitude spectrum of the ear canal microphone input signal. Predicting the output response may be performed using the output signal at the receiver and/or the external input signal. It is an advantage of this disclosure that the output response may be predicted despite the fact that the reference for measuring insertion gain, i.e. Real Ear Unaided Response (REUR), is unknown. Predicting the output response may be influenced by near-field effects when the ear canal or external microphone and receiver are in very close proximity to each other. It is seen as an advantage of the present disclosure that near-field effects are accounted for because the present disclosure allows the physical ear geometry to be estimated.

In one or more exemplary methods, determining a difference between the predicted output response and the ear canal microphone input signal comprises comparing the external input signal received at the external microphone and the measured ear canal microphone input signal received at the ear canal microphone. If the receiver and the ear canal microphone responses are known, the natural resonance of the open ear canal or the effect of occluding the ear can be accounted for. Alternatively, or additionally, the ear canal microphone response can be assumed as flat and the receiver response can be assumed as approximating the open ear response. With the disclosed method, the measured transducer response (receiver to ear canal microphone) may approximate the real ear unaided response (REUR).

In one or more exemplary methods, determining the difference may comprise predicting an insertion gain by comparing the signals at the external microphone and at the ear canal microphone, and subtracting the measured transducer response (receiver to ear canal microphone).

In one or more exemplary methods, obtaining the external input signal comprises determining one or more characteristics of the external input signal. For example, a characteristic may comprise a distortion and/or a spectrum, such as an amplitude (e.g. maximum amplitude) and/or a phase.

In one or more exemplary methods, obtaining the external input signal comprises determining one or more characteristics of the ear canal microphone input signal input signal in one or more frequency bands. For example, the one or more characteristics of the external input signal are measured or determined for each frequency band separately.

In one or more exemplary methods, obtaining the ear canal microphone input signal comprises measuring the ear canal microphone input signal indicative of the output signal as received by the ear canal microphone.

In one or more exemplary methods, measuring the ear canal microphone input signal comprises determining a forward pressure level of the measured ear canal microphone input signal. Sound pressure measured by an ear canal microphone can be decomposed into forward pressure level and reflected pressure level. Determining a forward pressure level of the measured ear canal microphone input signal leads to a measurement of the ear canal microphone input signal for the further derivation of the ear geometry.

In one or more exemplary methods, determining the difference between the predicted output response and the measured ear canal microphone input signal is based on one or more hearing device configuration parameters. For example, one or more hearing device configuration parameters may comprise a receiver placement, a receiver response, an external microphone placement, an external microphone response, an ear canal microphone placement, an ear canal microphone response, a presence of venting (opening or not), placement of opening if any, a dome and/or vent size, a dome and/or vent placement, and/or an expected device insertion depth.

In one or more exemplary methods, determining the difference between the predicted output response and the measured output is based on an initial hearing device calibration setting.

In one or more exemplary methods, determining the difference between the predicted output response and the measured output is based on one or more algorithm parameters. For example, the one or more algorithm parameters may be indicative of characteristics of the algorithm, such as interaction of spectral bands, non-linearity.

In one or more exemplary methods, the receiver is placed in an ear canal part of the hearing device. In one or more exemplary methods, the hearing device comprises an ear canal microphone and an ear canal receiver, where the ear canal microphone and the receiver are placed in the ear canal part of the hearing device. These exemplary methods may provide a real-ear insertion gain (REIG) that is flat for the user. In one or more exemplary method, determining a difference between the predicted output response and the measured ear canal microphone input signal may comprise measuring the difference in transfer function from the receiver to the open-ear (REUR) and from the receiver to the external microphone (L-MiE, Lateral Microphone). The relationship between REIG, the receiver response itself (RecToEar), L-MiE and the open-ear transfer function (REUR) may be expressed in the following way:

$$REIG=REAR-REUR$$

$$=L\text{-MiE}+RecToEar-REUR$$

$$=L\text{-MiE}-REUR+RecToEar$$

$$=RecToEar-(REUR-L\text{-MiE})$$

where REAR denotes real-ear aided response, i.e. the response when the hearing device is inserted in the ear canal of the user.

It can be seen that making the receiver response similar to the REUR−MiE response results in a flat insertion gain. The present disclosure allows a flat insertion gain to be obtained across a large number of customers and direction of arrival by just inserting the device into the ear canal. No extra equipment is needed.

In one or more exemplary methods, obtaining the external input signal comprises obtaining a specific measurement signal from an external device. The external input signal may be denoted an external microphone input signal.

The disclosed method may be performed when explicitly requested (e.g. by putting the hearing device in a calibration mode), and/or each time the device is turned on, and/or continuously.

A hearing device is disclosed. The hearing device may be a hearing aid, wherein the processor is configured to compensate for a hearing loss of a user.

The hearing device may be of the behind-the-ear (BTE) type, in-the-ear (ITE) type, in-the-canal (ITC) type, receiver-in-canal (RIC) type or receiver-in-the-ear (RITE) type. The hearing aid may be a binaural hearing aid. The hearing device may comprise a first earpiece and a second earpiece, wherein the first earpiece and/or the second earpiece is an earpiece as disclosed herein.

The hearing device may comprise an antenna for converting one or more wireless input signals, e.g. a first wireless input signal and/or a second wireless input signal, to an antenna output signal. The wireless input signal(s) origin from external source(s), such as spouse microphone device(s), wireless TV audio transmitter, and/or a distributed microphone array associated with a wireless transmitter.

The hearing device may comprise a transceiver, which may comprise a radio transceiver coupled to the antenna for converting the antenna output signal to a transceiver input signal. Wireless signals from different external sources may be multiplexed in the radio transceiver to a transceiver input signal or provided as separate transceiver input signals on separate transceiver output terminals of the radio transceiver. The hearing device may comprise a plurality of antennas and/or an antenna may be configured to be operate in one or a plurality of antenna modes. The transceiver input signal comprises a first transceiver input signal representative of the first wireless signal from a first external source.

The hearing device comprises a set of microphones. The set of microphones may comprise one or more microphones. The set of microphones comprises an external microphone for provision of an external input signal, and an ear canal microphone for obtaining an ear canal microphone input signal, which is based on the output signal transmitted by a receiver and received at the ear canal microphone. In other words, the ear canal microphone is configured to measure the ear canal microphone input signal.

The set of microphones may comprise one or more external microphones. The set of microphones may comprise one or more ear canal microphones. The set of microphones may comprise N microphones for provision of N microphone signals, wherein N is an integer in the range from 1 to 10. In one or more exemplary hearing devices, the number N of microphones is two, three, four, five or more. The set of microphones may comprise a third microphone for provision of a third microphone input signal.

In one or more exemplary hearing devices, the ear canal microphone may be positioned on the internal side of the hearing device (directed into the ear canal and facing the ear drum) and the external microphone may be positioned on the external side of the hearing device (capturing the environment). It is an advantage of the present disclosure to use these microphones, rather than a probe microphone, to measure the response inside the ear canal.

The hearing device comprises a processor for processing input signals and for providing a processed output signal based on input signals.

The hearing device comprises a receiver for transmission of an output signal and a controller configured to control hearing device settings. The hearing device is configured to estimate the ear geometry based on the external input signal and the ear canal microphone input signal.

The hearing device may be configured to estimate the ear geometry by predicting an output response based on the external input signal and gain settings of the hearing device. The hearing device may be configured to estimate the ear geometry by determining a difference between the predicted output response and the measured ear canal microphone input signal; and by estimating the ear geometry based on the difference.

In one or more exemplary hearing devices, the hearing device comprises a processing unit including the processor and the controller configured to control hearing device settings.

The present disclosure relates to a hearing device comprising an ear canal part (i.e. a part of the hearing device inserted in the ear canal of the ear) which may comprise an ear canal receiver and/or an ear canal microphone.

The present disclosure relates to a hearing-device receiver comprising a microphone-and-receiver-in-the-ear module, wherein the microphone-and-receiver in-the-ear module comprises an ear canal receiver and an ear canal microphone.

Throughout, the same reference numerals are used for identical or corresponding parts.

FIG. 1 is a block diagram of an exemplary hearing device according to the disclosure.

The hearing device 2 comprises a receiver 16 for transmission of an output signal 15. The receiver is configured to convert the output signal 15 into an audio output signal 11. The hearing device 2 comprises a set of microphones comprising an external microphone 8 for obtaining an external input signal 9 based a received signal 18 and providing the external input signal 9 to other modules of the hearing device 2.

The hearing device 2 comprises set of microphones. The set of microphones comprise an ear canal microphone 10 for obtaining an ear canal microphone input signal 11B, which is based on the audio signal 11A as received from a receiver 16. In other words, the ear canal microphone 10 may be configured to measure the audio signal 11A because the ear canal microphone 10 receives the audio signal 11A from the receiver 16, which is then passed on as an ear canal microphone input signal 11B. The audio output signal 11 is based on the output signal 15 provided by the processor 14. The audio output signal 11 is received as audio signal 11A at the ear canal microphone 10 is affected by the ear canal properties. This way, the disclosed hearing device is capable of estimating ear geometry, such as ear canal geometry.

The hearing device 2 comprises a controller 12 configured to control hearing device settings.

The hearing device 2 comprises a processor 14 for processing input signals and providing an output signal 15. The processor 14 may be connected to the controller 12 for receiving and processing signals. The processor 14 is configured to compensate for a hearing loss of a user and to provide an output signal 15.

The ear canal microphone 10 may be configured to provide ear microphone input signal 11B to the controller 12, and/or the processor 14.

The hearing device 2 may comprise an antenna 4 for converting a first wireless input signal 5 of a first external source (not shown in FIG. 1) to an antenna output signal. The hearing device 2 may comprise a transceiver 7 for provision of a transceiver input signal 3, which may comprise a radio transceiver coupled to the antenna 4 for converting the antenna output signal to one or more transceiver input signals.

In one or more exemplary hearing devices, the hearing device 2 comprises a processing unit 13 including the processor 14 and the controller 12. The processing unit 13 is configured to control hearing device parameters, to compensate for hearing loss.

A receiver 16 is configured to transmit an output signal 15 as an audio output signal 11 to be directed towards an eardrum of the hearing device user.

The hearing device 2 may comprise an ear canal part and another part towards the opening of the ear. In one or more exemplary hearing devices, the ear canal microphone 10 is positioned in the ear canal part of the hearing device 2, i.e. the part facing the ear drum or tympanic membrane) and the external microphone 8 is positioned on the part of the hearing device 2 that faces the opening of the ear (capturing the environment).

The hearing device 2 or the processor 14 is configured to predict an output response based on the external input signal 9 and the gain settings. The hearing device 2 or the processor 14 may be configured to predict an output response based on the external input signal 9, the output signal 15 and the gain settings. The hearing device 2 or the processor 14 is configured to determine a difference between the predicted output response and ear canal microphone input signal 11B.

In one or more exemplary hearing devices, the processing unit 13 is configured to predict an output response based on the external input signal 9 and gain settings of the hearing device and to determine a difference between the predicted output response and the ear canal microphone input signal 11B.

In one or more exemplary hearing devices, determining a difference between the predicted output response and the ear canal microphone input signal 11B comprises comparing the external input signal 9 received at the external microphone 8 and the ear canal microphone input signal 11B from the ear canal microphone 10. The hearing device 2 may be configured to determine the difference between the predicted output response and the ear canal microphone input signal 11B by estimating an ear parameter such as the ear canal length. As a length resonance results in a spectral notch in the output response at the ear canal microphone 10, and the frequency of this notch varies with the residual ear canal length, the hearing device 2 determines the ear canal length based on identification of the frequency of the notch and categorization of the frequency. Once the frequency of the notch of the output response at the ear canal microphone is identified, a canal length that is expected to result in a notch at this frequency is determined using the category. The hearing device 2 may determine an appropriate real-ear insertion gain (REIG) correction for the ear canal based on an expected spectral difference between the locations of the ear canal microphone 8 and the tympanic membrane. To correct the insertion gain, the hearing device 2 may be configured to apply the inverse of the predicted real-ear insertion gain, such as applying half of the predicted real-ear insertion gain.

The hearing device 2 may be configured to categorize an ear canal. The hearing device 2 may be configured to determine one or more ear canal parameters, such as one or more of an ear canal volume, an ear canal width, an ear canal length, and an ear canal conicity.

The hearing device 2 may be configured to determine one or more ear canal parameters based on an estimate of real-ear unaided gain, and/or user input.

The external microphone 8 may be configured to obtain the external input signal by determining one or more characteristics of the external input signal, such as in one or more frequency bands.

The ear canal microphone 10 may be configured to obtain the ear microphone input signal by determining one or more characteristics of ear canal microphone input signal, such as by measuring the ear canal microphone input signal indicative of the output signal as received by the ear canal microphone. For example, measuring the ear canal microphone input signal may comprise determining a forward pressure level of the ear canal microphone input signal.

Figure 2:
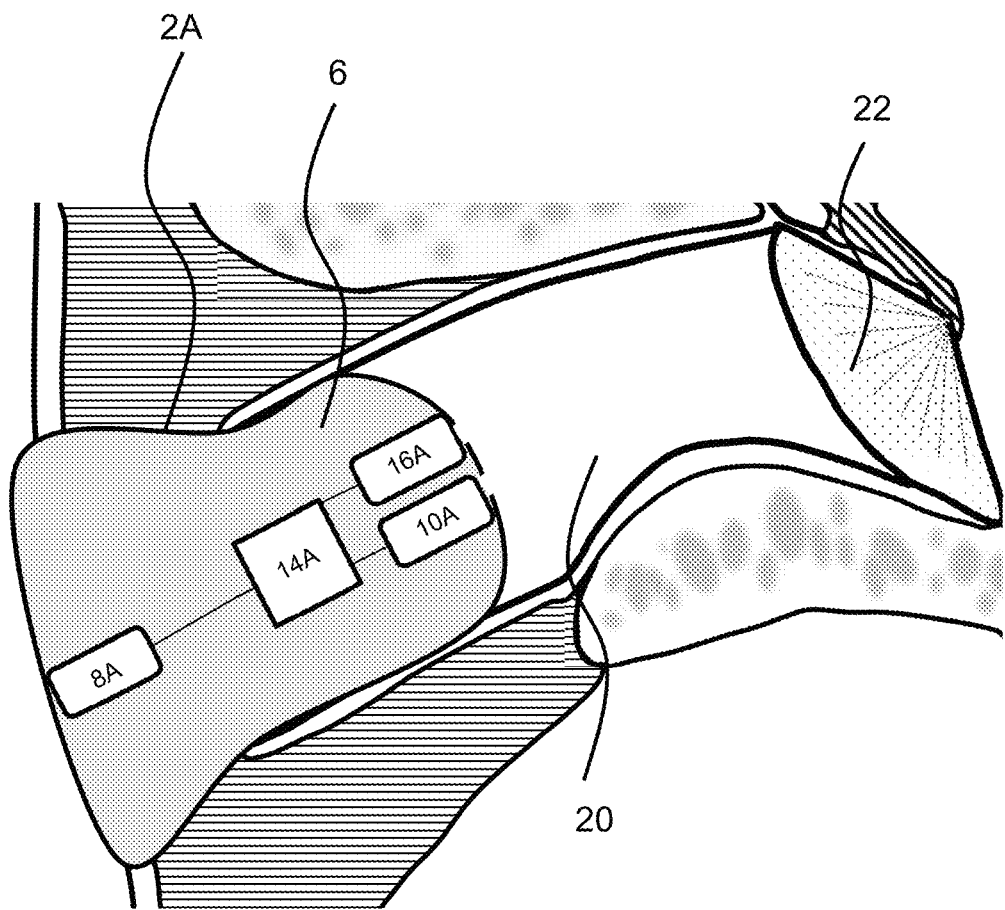

FIG. 2 is a cross-section of a user's ear having an exemplary hearing device 2A partly inserted in the ear canal 20 of the ear according to the disclosure. The hearing device 2A is an in-the-ear hearing device. The hearing device 2A comprises a housing 6, a receiver 16A, an external microphone 8A for obtaining an input signal and an ear canal microphone 10A. The receiver 16A is placed in an ear canal part of the hearing device 2A, and thereby called an ear canal receiver 16A. The hearing device 2A comprises the ear canal microphone 10A and the ear canal receiver 16A, which are placed facing the ear drum or tympanic membrane 22. The hearing device 2A comprises a processor 14A configured to compensate for a hearing loss of a user. The receiver 16A is configured to transmit an output signal to be directed towards an eardrum of the hearing device user. The ear canal microphone 10A is configured to obtain an ear canal microphone input signal 11B based on the output signal received from the receiver 16A because the ear canal microphone 10A receives the output signal from the receiver 16A as an ear canal microphone input signal. The output signal received as input at the ear canal microphone 10A is affected by the ear canal properties. The processor 14A is configured to estimate the ear geometry based on the external input signal and the ear canal microphone input signal by e.g.: predicting an output response based on the external microphone input signal and gain settings, determining a difference between the predicted output response and the ear canal microphone input signal, and estimating the ear geometry based on the difference. In one or more exemplary hearing devices, determining a difference between the predicted output response and the ear canal microphone input signal comprises comparing the input signal received at the external microphone and the ear canal microphone input signal at the ear canal microphone.

Figure 3:
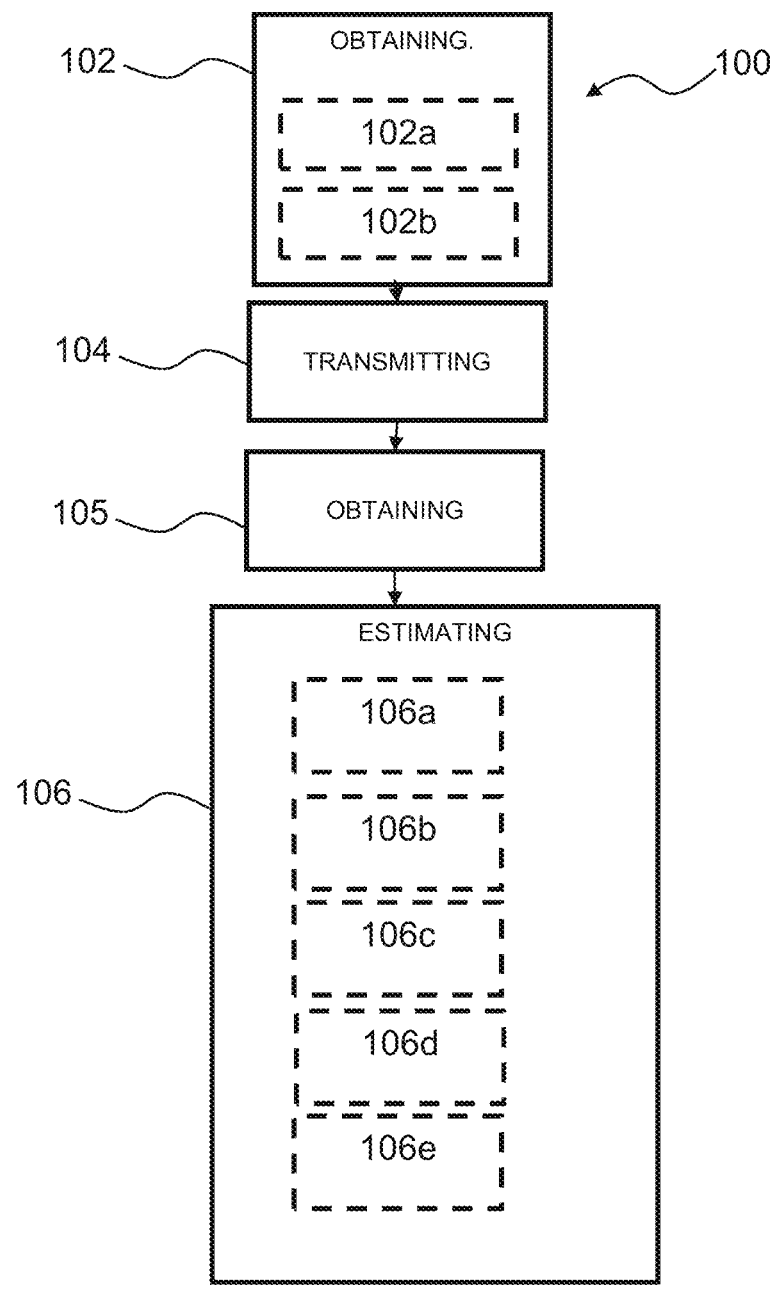
FIG. 3 is a flow diagram of an exemplary method according to the disclosure.

FIG. 3 shows a flow diagram of an exemplary method of estimating an ear geometry of an ear of a hearing device user with a hearing device. The hearing device comprises an ear canal microphone, an external microphone and a receiver. The method comprises obtaining 102 an external input signal with the external microphone, such as using the external microphone.

In one or more methods, obtaining 102 an external input signal with the external microphone comprises measuring 102a the external input signal using the external microphone, e.g. using the external microphone and analysing the external input signal.

The method 100 comprises transmitting 104 an output signal with the receiver and obtaining 105 an ear canal microphone input signal using the ear canal microphone. In one or more exemplary methods, ear canal microphone input signal may be a specific measurement signal and/or an environmental signal.

The method 100 comprises estimating 106 an ear geometry based on the external input signal and the ear canal microphone input signal.

In one or more exemplary methods, estimating 106 an ear geometry comprises predicting 106a an output response based on the external input signal and the gain settings of the hearing device, and/or optionally device calibration (such as factory or default device calibration). Estimating 106 an ear geometry may comprise determining 106b a difference between the predicted output response and the ear canal microphone input signal, and estimating 106c the ear geometry based on the difference.

In one or more exemplary methods, estimating 106 an ear geometry comprises categorizing 106d an ear canal. For example, one or more categories may be predetermined. A plurality of categories may lead to more accuracy in estimating the ear geometry. Categorizing an ear may be performed based on the ear canal parameter. It may also be seen that categorizing an ear comprises estimating the ear geometry.

In one or more exemplary methods, estimating 106 the ear geometry comprises determining 106e an ear canal parameter. The ear canal parameter may comprise one or more of an ear canal volume, an ear canal width, an ear canal length, and an ear canal conicity.

In one or more exemplary methods, determining 106e the ear canal parameter is based on an estimate of real-ear unaided gain, user input and/or acoustic measurement. In determining the difference between the predicted output response and the measured ear canal microphone input signal, the inventors have determined that a length resonance often results in a spectral notch in the output response at the ear canal microphone, and the frequency of this notch varies with the residual ear canal length. The ear canal length can thereby be determined. Once the frequency of the notch of the output response at the ear canal microphone is identified, a canal length that is expected to result in a notch at this frequency is determined using the category. An appropriate real-ear insertion gain (REIG) correction for this ear canal may be determined based on an expected spectral difference between the locations of the ear canal microphone and the tympanic membrane. To correct the insertion gain, the method may comprise applying the inverse of the predicted real-ear insertion gain (assuming target gain is 0 dB). Because predictions may not be perfect, a fraction of the predicted real-ear insertion gain may be used as a conservative correction. If the target gain is not a flat (e.g. 0 dB at all frequencies), the target gain may be subtracted from the predicted gain before using it as a correction factor.

In one or more exemplary methods, determining 106b a difference between the predicted output response and the ear canal microphone input signal comprises determining a difference between the predicted output magnitude spectrum and the measured output magnitude spectrum. Predicting 106a the output response may be performed using the output signal as transmitted by the receiver.

In one or more exemplary methods, determining 106b a difference between the predicted output response and the ear canal microphone input signal comprises comparing the external input signal received at the external microphone and the ear canal microphone input signal at the ear canal microphone. If the receiver and the ear canal microphone responses are known, the natural resonance of the open ear canal or the effect of occluding the ear can be accounted for. Alternatively, or additionally, the ear canal microphone response can be assumed as flat and the receiver response can be assumed as approximating the open ear response. With the disclosed method, the measured transducer response (receiver to ear canal microphone) may approximate the real ear unaided response (REUR).

In one or more exemplary methods, determining 106b the difference may comprise determining an insertion gain by comparing the signals at the external microphone and at the ear canal microphone, and subtracting the measured transducer response (receiver to ear canal microphone).

In one or more exemplary methods, obtaining 102 the external input signal comprises determining 102b one or more characteristics of the external input signal, such as in one or more frequency bands. For example, a characteristic may comprise a distortion and/or a spectrum, such as an amplitude (e.g. maximum amplitude) and/or a phase.

In one or more exemplary methods, obtaining 105 the ear canal microphone input signal comprises determining a forward pressure level of the ear canal microphone input signal. Sound pressure measured by an ear canal microphone can be decomposed into forward pressure level and reflected pressure level. The present disclosure relates to determining the forward pressure level of the ear canal microphone input signal.

In one or more exemplary methods, determining 106b the difference between the predicted output response and the ear canal microphone input signal is based on one or more hearing device configuration parameters.

In one or more exemplary methods, determining 106b the difference between the predicted output response and the ear canal microphone input signal is based on an initial hearing device calibration setting.

In one or more exemplary methods, determining 106b the difference between the predicted output response and the ear canal microphone input signal is based on one or more algorithm parameters. For example, the one or more algorithm parameters may be indicative of characteristics of the algorithm, such as interaction of spectral bands, non-linearity.

In one or more exemplary methods, determining 106b the difference between the predicted output response and the ear canal microphone input signal may comprise estimating other parameters of the ear canal, such as one or more tympanic membrane properties. Determining the difference between the predicted output response and the measured ear canal microphone input signal may take into account ear canal dimensions (e.g. user-supplied information about ear canal geometry (e.g., large/small, male/female, head circumference, etc.)) and/or hearing device configurations. Predicting ear canal dimensions may be performed based on acoustic measurements according to this disclosure.

In one or more exemplary methods, predicting 106a the output response is based on the initial hearing device calibration setting.

In one or more exemplary methods, obtaining 102 the external input signal comprises obtaining a specific measurement signal from an external device.

The use of the terms "first", "second", "third" and "fourth", etc. does not imply any order, but are included to identify individual elements. Moreover, the use of the terms first, second, etc. does not denote any order or importance, but rather the terms first, second, etc. are used to distinguish one element from another. Note that the words first and second are used here and elsewhere for labelling purposes only and are not intended to denote any specific spatial or temporal ordering. Furthermore, the labelling of a first element does not imply the presence of a second element and vice versa.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 hearing device
2A hearing device seen from a cross-section
3 transceiver input signal
4 antenna
5 first wireless input signal
6 housing
7 radio transceiver
8 external microphone
8A external microphone
9 external input signal from external microphone
10 ear canal microphone
10A ear canal microphone
11 audio output signal emitted by the receiver
11A audio signal received as input at the ear canal microphone
11B ear canal microphone input signal
12 controller
13 processing unit
14 processor
14A processor
15 output signal
16 receiver
16A ear canal receiver
18 audio signal obtained at the external microphone
20 ear canal
22 ear drum or tympanic membrane
100 method of estimating ear geometry
102 obtaining an external input signal
102a measuring the external input signal
102b determining one or more characteristics of the external input signal
104 transmitting an output signal with the receiver and measuring 105 the output signal using the ear canal microphone
105 obtaining the ear canal microphone signal using the ear canal microphone
106 estimating the ear geometry
106a predicting an output response based on gain settings
106b determining a difference between the predicted output response and the ear canal microphone input signal
106c estimating an ear geometry based on the difference
106d categorizing an ear
106e determining an ear canal parameter

The invention claimed is:

1. A method for estimating an ear geometry of an ear of a user with a hearing device, the hearing device comprising an ear canal microphone, an external microphone, and a receiver, the method comprising:
obtaining an external input signal using the external microphone;
providing an output signal by the receiver;
obtaining an ear canal microphone input signal using the ear canal microphone; and
estimating the ear geometry based on the external input signal and the ear canal microphone input signal;
wherein the act of estimating the ear geometry is performed based on hearing device configuration parameter(s) comprising an ear canal microphone response and/or a receiver response; and
wherein the ear canal microphone response comprises a flat ear canal microphone response.

2. The method according to claim 1, wherein the act of estimating the ear geometry comprises:
predicting an output response based on the external input signal and gain setting(s) of the hearing device;
determining a difference between the predicted output response and the ear canal microphone input signal; and
estimating the ear geometry based on the difference.

3. The method according to claim 1, wherein the act of estimating the ear geometry comprises categorizing an ear canal.

4. The method according to claim 1, wherein the act of estimating the ear geometry comprises determining one or more ear canal parameters.

5. The method according to claim 4, wherein the one or more ear canal parameters comprises an ear canal volume, an ear canal width, an ear canal length, an ear canal conicity, or any combination of the foregoing.

6. The method according to claim 4, wherein the one or more ear canal parameter is determined based on an estimate of real-ear unaided gain, and/or user input.

7. The method according to claim 1, wherein the act of obtaining the external input signal comprises determining one or more characteristics of a signal.

8. The method according to claim 1, wherein the act of obtaining the external input signal comprises determining one or more characteristics of a signal in one or more frequency bands.

9. The method according to claim 1, wherein the act of obtaining the ear canal microphone input signal comprises generating the ear canal microphone input signal by the ear canal microphone.

10. The method according to claim 9, wherein the ear canal microphone input signal is generated in response to the output signal received by the ear canal microphone.

11. The method according to claim 1, wherein the act of obtaining the ear canal microphone input signal comprises determining a forward pressure level of the ear canal microphone input signal.

12. The method according to claim 2, wherein the act of determining the difference between the predicted output response and the ear canal microphone input signal is performed based on the hearing device configuration parameter(s).

13. The method according to claim 2, wherein the act of determining the difference between the predicted output response and the ear canal microphone input signal is performed based on an initial hearing device calibration setting.

14. The method according to claim 1, wherein the receiver is in an ear canal part of the hearing device.

15. The method according to claim 1, wherein the act of obtaining the external input signal is performed in response to a measurement signal provided by an apparatus.

16. The method according to claim 1, wherein the receiver response corresponds with an open ear response; and
wherein the act of estimating the ear geometry is performed based on the flat ear canal microphone response and the receiver response corresponding with the open ear response.

17. The method according to claim 1, wherein the act of estimating the ear geometry comprises estimating one or more of: an ear shape, an ear dimension, an ear canal dimension, an ear canal volume, an ear canal conicity, or an ear canal type, based on the flat ear canal microphone response.

18. The method according to claim 1, wherein the flat ear canal microphone response is an assumed response.

19. A hearing device comprising:
a receiver for providing of an output signal;
an external microphone for providing an external input signal;
an ear canal microphone for providing an ear canal microphone input signal; and
a processing unit comprising a hardware component;
wherein the processing unit of the hearing device is configured to estimate an ear geometry based on the external input signal and the ear canal microphone input signal;
wherein the processing unit of the hearing device is configured to estimate the ear geometry based on hearing device configuration parameter(s) comprising an ear canal microphone response and/or a receiver response; and
wherein the ear canal microphone response comprises a flat ear canal microphone response.

20. The hearing device according to claim 19, wherein the hearing device is configured to estimate the ear geometry by:
predicting an output response based on the external input signal and gain setting(s) of the hearing device;
determining a difference between the predicted output response and the ear canal microphone input signal; and
estimating the ear geometry based on the difference.

21. The hearing device according to claim 20, wherein the hearing device is configured to determine the difference between the predicted output response and the ear canal microphone input signal based on the hearing device configuration parameter(s).

22. The hearing device according to claim 20, wherein the hearing device is configured to determine the difference between the predicted output response and the ear canal microphone input signal based on an initial hearing device calibration setting.

23. The hearing device according to claim 19, wherein the hearing device is configured to estimate the ear geometry by categorizing an ear canal and/or determining one or more ear canal parameters.

24. The hearing device according to claim 19, wherein the receiver response corresponds with an open ear response; and
wherein the hearing device is configured to estimate the ear geometry based on the flat ear canal microphone response and the receiver response corresponding with the open ear response.

25. The hearing device according to claim 19, wherein the processing unit of the hearing device is configured to estimate the ear geometry by estimating one or more of: an ear shape, an ear dimension, an ear canal dimension, an ear canal volume, an ear canal conicity, or an ear canal type, based on the flat ear canal microphone response.

26. The hearing device according to claim 19, wherein the flat ear canal microphone response is an assumed response.

27. A method for estimating an ear geometry of an ear of a user with a hearing device, the hearing device comprising an ear canal microphone, an external microphone, and a receiver, the method comprising:
obtaining an external input signal using the external microphone;
providing an output signal by the receiver;
obtaining an ear canal microphone input signal using the ear canal microphone; and
estimating the ear geometry based on the external input signal and the ear canal microphone input signal;
wherein the ear geometry is estimated also based on an ear canal microphone response that is modeled as flat.

28. A hearing device comprising:
a receiver for providing of an output signal;
an external microphone for providing an external input signal;
an ear canal microphone for providing an ear canal microphone input signal; and
a processing unit comprising a hardware component;
wherein the processing unit of the hearing device is configured to estimate an ear geometry based on the external input signal and the ear canal microphone input signal; and
wherein the processing unit of the hearing device is configured to estimate the ear geometry based on an ear canal microphone response that is modeled as flat.

* * * * *